US009549713B2

(12) United States Patent
Sathyanarayana et al.

(10) Patent No.: US 9,549,713 B2
(45) Date of Patent: Jan. 24, 2017

(54) METHODS, SYSTEMS, AND DEVICES FOR TISSUE CHARACTERIZATION AND QUANTIFICATION USING INTRAVASCULAR ULTRASOUND SIGNALS (75) Inventors: Shashidhar Sathyanarayana, Pleasanton, CA (US); Wenguang Li, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2054 days.

(21) Appl. No.: 12/563,754

(22) Filed: Sep. 21, 2009

(65) Prior Publication Data

US 2010/0022880 A1 Jan. 28, 2010

Related U.S. Application Data (63) Continuation-in-part of application No. 12/429,005, filed on Apr. 23, 2009, now abandoned.
(Continued)

(51) Int. Cl.
*A61B 8/00* (2006.01)
*A61B 8/08* (2006.01)
(Continued)

(52) U.S. Cl.
CPC ............ *A61B 8/08* (2013.01); *A61B 5/02007* (2013.01); *A61B 5/7264* (2013.01); *A61B 8/12* (2013.01);
(Continued)

(58) Field of Classification Search
CPC . A61B 5/7267; A61B 5/7264; A61B 5/02007; A61B 8/08; A61B 8/12; G06K 9/00147
(Continued)

(56) References Cited

U.S. PATENT DOCUMENTS 4,817,015 A 3/1989 Insana et al.
4,858,124 A 8/1989 Lizzi et al.
(Continued)

FOREIGN PATENT DOCUMENTS

EP 1239774 9/2002
EP 1739593 1/2007
(Continued)

OTHER PUBLICATIONS

Andrew L. McLeod et al, Classification of Arterial Plaque by Spectral Analysis in Remodelled Human Atherosclerotic Coronary Arteries, Ultrasound in Med. & Biol., vol. 30, No. 2, pp. 155-159, 2004.*
(Continued)

*Primary Examiner* — Serkan Akar
(74) *Attorney, Agent, or Firm* — Lowe Graham Jones PLLC; Bruce E. Black (57) ABSTRACT

A method of evaluating at least one tissue type includes providing a tissue classifier comprising multiple detector arrays for each of multiple tissue types. Each detector array comprises multiple detectors and each detector comprises multiple tissue type-assigned intravascular ultrasound (IVUS) spectra. For each of the detector arrays, an input IVUS spectrum of the tissue region is compared to the tissue type-assigned IVUS spectra of each of the detectors in the detector array and it is determined whether the input spectrum corresponds to the tissue type of the detector. The results for the detector. The results for the detector arrays are combined to provide a tissue characterization of the tissue region from the multiple tissue types. One or more IVUS images can be displayed with the tissue characterization and an indication of the size of at least one of the tissue types in a selected portion of the image that is displayed.

22 Claims, 6 Drawing Sheets

Related U.S. Application Data (60) Provisional application No. 61/047,575, filed on Apr. 24, 2008.

(51) Int. Cl.
*A61B 5/02* (2006.01)
*A61B 5/00* (2006.01)
*A61B 8/12* (2006.01)
*G06K 9/00* (2006.01)

(52) U.S. Cl.
CPC ......... *G06K 9/00147* (2013.01); *A61B 5/7267* (2013.01)

(58) Field of Classification Search
USPC ........................................................ 600/443
See application file for complete search history.

(56) References Cited

U.S. PATENT DOCUMENTS

| | | | |
|---|---|---|---|
| 5,081,993 | A | 1/1992 | Kitney et al. |
| 5,497,770 | A | 3/1996 | Morcos et al. |
| 6,019,724 | A | 2/2000 | Gronningsaeter et al. |
| 6,192,360 | B1 | 2/2001 | Dumais et al. |
| 6,200,268 | B1 | 3/2001 | Vince et al. |
| 6,238,342 | B1 | 5/2001 | Feleppa et al. |
| 6,945,938 | B2 | 9/2005 | Grunwald |
| 7,074,188 | B2 | 7/2006 | Nair et al. |
| 7,175,597 | B2 | 2/2007 | Vince et al. |
| 7,245,789 | B2 | 7/2007 | Bates et al. |
| 7,306,561 | B2 | 12/2007 | Sathyanarayana |
| 7,447,388 | B2 | 11/2008 | Bates et al. |
| 7,672,706 | B2 | 3/2010 | Sathyanarayana |
| 7,729,533 | B2* | 6/2010 | Sathyanarayana ............ 382/159 |
| 7,892,175 | B2 | 2/2011 | Wakabayashi et al. |
| 2003/0220556 | A1 | 11/2003 | Porat et al. |
| 2004/0067000 | A1 | 4/2004 | Bates et al. |
| 2004/0146201 | A1 | 7/2004 | Sathyanarayana |
| 2004/0254463 | A1 | 12/2004 | Lehman |
| 2005/0043614 | A1 | 2/2005 | Huizenga et al. |
| 2005/0065426 | A1 | 3/2005 | Porat et al. |
| 2005/0154315 | A1 | 7/2005 | Nair et al. |
| 2005/0228254 | A1 | 10/2005 | Torp et al. |
| 2005/0249391 | A1 | 11/2005 | Kimmel et al. |
| 2005/0251116 | A1 | 11/2005 | Steinke et al. |
| 2006/0041199 | A1 | 2/2006 | Elmaleh et al. |
| 2006/0056703 | A1 | 3/2006 | Sathyanarayana |
| 2006/0100522 | A1 | 5/2006 | Yuan et al. |
| 2006/0120608 | A1 | 6/2006 | Luo et al. |
| 2006/0173350 | A1 | 8/2006 | Yuan et al. |
| 2006/0222221 | A1 | 10/2006 | Sathyanarayana |
| 2006/0235286 | A1 | 10/2006 | Stone et al. |
| 2006/0253028 | A1 | 11/2006 | Lam et al. |
| 2006/0271040 | A1 | 11/2006 | Horne et al. |
| 2006/0277998 | A1 | 12/2006 | Masotti |
| 2007/0003116 | A1 | 1/2007 | Yuan et al. |
| 2007/0005356 | A1 | 1/2007 | Perronnin |
| 2007/0016054 | A1 | 1/2007 | Cao et al. |
| 2007/0038111 | A1 | 2/2007 | Rehrig et al. |
| 2007/0049827 | A1 | 3/2007 | Donaldson |
| 2007/0055153 | A1 | 3/2007 | Simopoulos et al. |
| 2007/0078500 | A1 | 4/2007 | Ryan et al. |
| 2007/0083111 | A1 | 4/2007 | Hossack et al. |
| 2007/0100239 | A1 | 5/2007 | Nair et al. |
| 2007/0127789 | A1 | 6/2007 | Hoppel et al. |
| 2007/0133925 | A1 | 6/2007 | Bates et al. |
| 2007/0160275 | A1 | 7/2007 | Sathyanarayana |
| 2007/0165920 | A1 | 7/2007 | Gering et al. |
| 2007/0237371 | A1 | 10/2007 | Zhu et al. |
| 2007/0260141 | A1 | 11/2007 | Margolis et al. |
| 2007/0265521 | A1 | 11/2007 | Redel et al. |
| 2007/0282202 | A1 | 12/2007 | Maurice et al. |
| 2007/0299343 | A1 | 12/2007 | Waters |
| 2008/0039830 | A1 | 2/2008 | Munger et al. |
| 2008/0063265 | A1* | 3/2008 | Sathyanarayana ............ 382/159 |
| 2008/0125772 | A1 | 5/2008 | Stone et al. |
| 2008/0234582 | A1 | 9/2008 | Nair et al. |
| 2008/0312673 | A1 | 12/2008 | Viswanathan et al. |
| 2009/0059727 | A1 | 3/2009 | Bates et al. |
| 2009/0105579 | A1 | 4/2009 | Garibaldi |
| 2009/0137952 | A1 | 5/2009 | Ramamurthy et al. |
| 2009/0299195 | A1 | 12/2009 | Muller et al. |

FOREIGN PATENT DOCUMENTS

| | | |
|---|---|---|
| EP | 1780672 | 5/2007 |
| WO | 94/23652 | 10/1994 |
| WO | 9519135 | 7/1995 |
| WO | 9625881 | 8/1996 |
| WO | 9625882 | 8/1996 |
| WO | 98/24065 | 6/1998 |
| WO | 9967728 | 12/1999 |
| WO | 03/075770 | 9/2003 |
| WO | 03096872 | 11/2003 |
| WO | 2004032746 | 4/2004 |
| WO | 2005033738 | 4/2005 |
| WO | 2005/071615 | 8/2005 |
| WO | 2005070300 | 8/2005 |
| WO | 2005074804 | 8/2005 |
| WO | 2005107623 | 11/2005 |
| WO | 2006/042077 | 4/2006 |
| WO | 2006105121 | 10/2006 |
| WO | 2006110830 | 10/2006 |
| WO | 2007041542 | 4/2007 |
| WO | 2007047404 | 4/2007 |
| WO | 2007047566 | 4/2007 |
| WO | 2007109771 | 9/2007 |
| WO | 2008022148 | 2/2008 |
| WO | 2008049084 | 4/2008 |
| WO | 2008107905 | 9/2008 |
| WO | 2009/023626 | 2/2009 |
| WO | 2009023801 | 2/2009 |

OTHER PUBLICATIONS

Ren Kawaguchi et al. Usefulness of Virtual Histology Intravascular Ultrasound to Predict Distal Embolization for ST-Segment Elevation Myocardial Infarction, Journal of the American College of Cardiology vol. 50, No. 17, 2007.*
Watson et al, "Classification of Arterial Plaque by Spectral Analysis of In Vitro Radio Frequency Intra Vascular Ultrasound Data", UltraSound in Med. & Biol., vol. 26, No. I. pp. 73-80, 2000.*
Official Communication for U.S. Appl. No. 12/429,005 mailed Nov. 9, 2011.
Official Communication for U.S. Appl. No. 12/429,005 mailed Jun. 10, 2011.
Kittler, J. et al., "On Combining Classifiers," IEEE Transactions on Pattern Analysis and Machine Intelligence, Mar. 1998, 20(3):226-239.
Watson, R. J. et al. "Classification of Arterial Plaque by Spectral Analysis of In Vitro Radio Frequency Intravascular Ultrasound Data." Ultrasound in Medicine and Biology. vol. 26, No. 1, p. 73-80 (2000).
Sarkar, M. "Modular Pattern Classifiers: A Brief Survey." Systems, Man, and Cybernetics, 2000 IEEE International Conference on Nashville, TN, USA. vol. 4, pp. 2878-2883 (2000).
Caballero, et al., "Using Reconstructed IVUS Images for Coronary Plaque Classification," Proceedings of the 29th Annual International Conference of the IEEE EMBS, Aug. 23-26, pp. 2167-2170 (2007).
U.S. Appl. No. 12/429,00, Official Communication mailed Feb. 14, 2012.
U.S. Appl. No. 12/429,005, Official Communication mailed Apr. 5, 2012.
U.S. Appl. No. 12/429,005, Official Communication mailed Jun. 29, 2012.
U.S. Appl. No. 12/429,005, Official Communication mailed Mar. 21, 2013.

* cited by examiner

METHODS, SYSTEMS, AND DEVICES FOR TISSUE CHARACTERIZATION AND QUANTIFICATION USING INTRAVASCULAR ULTRASOUND SIGNALS

RELATED APPLICATIONS

This application is a continuation-in-part of U.S. patent application Ser. No. 12/429,005, filed Apr. 23, 2009, which claims the benefit of U.S. Provisional Patent Application No. 61/047,575, filed Apr. 24, 2008, both of which are incorporated herein by reference.

TECHNICAL FIELD

The present invention is directed to the area of intravascular ultrasound (IVUS) imaging systems and devices and methods of making and using the systems and devices. The present invention is also directed to methods, systems, and devices for tissue characterization using IVUS signals.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

One embodiment is a method of evaluating at least one tissue type in at least one intravascular ultrasound (IVUS) image including providing a tissue classifier comprising a plurality of detector arrays for each of a plurality of tissue types, where each detector array comprises a plurality of detectors and each detector comprises a plurality of tissue type-assigned IVUS spectra. A plurality of the tissue type-assigned IVUS spectra of each detector correspond to a tissue type of the detector and a plurality of the tissue type-assigned IVUS spectra correspond to other tissue types. The method continues by comparing an input IVUS spectrum of a region in the at least one intravascular ultrasound image to the tissue type-assigned IVUS spectra of each of the plurality of detectors for each of the plurality of detector arrays. For each of the plurality of detectors of each of the plurality of detector arrays, it is determined whether the input spectrum corresponds to the tissue type of the detector based on the comparisons of the input spectrum to the tissue type-assigned spectra for that detector. For each of the plurality of detector arrays, results of the plurality of detectors of the detector array are combined to produce an array result. The array results are combined for the plurality of detector arrays to provide a tissue characterization of the region from the plurality of tissue types. This is repeated for each region to be characterized in the at least one intravascular ultrasound image. A size of at least one of the tissue types in a selected portion of the at least one intravascular ultrasound image is determined using the tissue characterizations of the regions in the selected portion. One or more of the at least one intravascular ultrasound image can be displayed with an indication of the tissue characterization of one or more regions of the at least one intravascular ultrasound image that is displayed and an indication of the size of at least one of the tissue types in the selected portion of the at least one intravascular ultrasound image that is displayed.

Another embodiment is a computer-readable medium having processor-executable instructions for characterizing tissue. The processor-executable instructions when installed onto a device enable the device to perform the method described above.

Yet another embodiment is a tissue classifier that includes multiple detector arrays for each of multiple tissue types. Each detector array comprises multiple detectors and each detector comprises multiple tissue type-assigned intravascular ultrasound (IVUS) spectra. A plurality of the tissue type-assigned IVUS spectra of each detector correspond to a tissue type of the detector and a plurality of the tissue type-assigned IVUS spectra correspond to other tissue types. The tissue classifier also includes a processor for executing processor-readable instructions that enable actions including the following: For each of the detector arrays, an input IVUS spectrum of the tissue region is compared to an input IVUS spectrum of a region in the at least one intravascular ultrasound image to the tissue type-assigned IVUS spectra of each of the plurality of detectors. For each of the plurality of detectors of each of the plurality of detector arrays, it is determined whether the input spectrum corresponds to the tissue type of the detector based on the comparisons of the input spectrum to the tissue type-assigned spectra for that detector. For each of the plurality of detector arrays, results of the plurality of detectors of the detector array are combined to produce an array result. The array results are combined for the plurality of detector arrays to provide a tissue characterization of the region from the plurality of tissue types. This is repeated for each region to be characterized in the at least one intravascular ultrasound image. A size of at least one of the tissue types in a selected portion of the at least one intravascular ultrasound image is determined using the tissue characterizations of the regions in the selected portion. One or more of the at least one intravascular ultrasound image can be displayed with an indication of the tissue characterization of one or more regions of the at least one intravascular ultrasound image that is displayed and an indication of the size of at least one of the tissue types in the selected portion of the at least one intravascular ultrasound image that is displayed.

A further embodiment is an imaging device that includes the tissue classifier described above, as well as a catheter for insertion into a patient; a transducer disposed on the catheter to produce ultrasound signals and receive backscattered signals; and a processor coupled to the transducer to receive the backscattered signals from the transducer and to generate an image from the backscattered signals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of intravascular ultrasound (IVUS) imaging systems and devices and methods of making and using the systems and devices. The present invention is also directed to methods, systems, and devices for tissue characterization using IVUS signals. It will be understood that the methods described herein can also be applied to imaging techniques other than IVUS.

Conventional tissue characterization methods include those that deduce and present information on tissue type using mathematical algorithms that operate directly on radiofrequency (RF) ultrasound data. For example, some techniques are based on analyzing the frequency content of RF data.

In contrast, a process, system, or device, incorporating a tissue classifier as described herein, can be used to infer tissue type from an input spectrum based on comparison to spectra from a large number of samples of each tissue type of clinical interest. The process, system, or device can characterize tissue type on the basis of differing spectral signatures which are caused by differences in acoustic properties of tissue which in turn could arise from differing pathology. Different tissue types typically absorb and backscatter the various frequencies of ultrasound energy differently, giving rise to different frequency spectra.

The tissue characterization techniques described herein include preparing a tissue classifier for testing an input spectrum for spectral similarity to known tissue type-assigned spectra. The tissue classifier may be calibrated (trained) against spectra of known tissue types that have been determined through, for example, histological analysis. In at least some embodiments, a color-coded tissue map can be generated with the various tissue types labeled in specific colors. Other methods for providing the tissue classification to a practitioner can also be used.

Preparation of an IVUS tissue characterization system or device includes obtaining or preparing a set of ultrasound spectra that have been established to have originated from tissue of known type. A tissue classifier can be prepared, as disclosed herein, to classify any selected number of tissue types including, for example, two, three, four, five, six, seven, eight, ten, or more types of tissue. A specific example for four types of tissue (necrotic, lipidic, calcified, and fibrotic tissue) will be described herein to illustrate the methods and systems. It will be understood that the methods, devices, and systems described herein can be used with other selections of tissue types.

The spectrum of the radiofrequency backscatter signal corresponding to a location on an IVUS image is used to determine tissue type. Any technique for obtaining an IVUS image, or the corresponding IVUS backscatter signals, can be used. In at least some embodiments, the IVUS image is obtained using a transducer disposed in a catheter that is introduced into the blood vessel or other tissue that is to be imaged. The transducer is coupled to a control unit that directs the transducer to emit an ultrasonic pulse of energy. The ultrasonic energy travels to the tissue where a portion of the energy is backscattered. The backscattered energy is detected by the transducer as the IVUS signal. The temporal dimension of the IVUS signal is used to locate the tissue as a function of distance from the transducer. The further the tissue is away from the transducer, the longer it will take for the ultrasound signal to travel to the tissue and be scattered back to the transducer. A temporally windowed portion of the backscattered signal that corresponds to a desired location can then be selected and used to determine the frequency spectrum of the tissue at that location. The frequency spectrum can be determined from the IVUS backscatter signal using, for example, fast Fourier transform techniques or the like.

Typically, the transducer directs the ultrasound pulse, and obtains an IVUS signal, for only a relatively small region of the surrounding tissue at any given time. After receiving the backscattered signal from one region of a vessel or tissue, the transducer is rotated (e.g., by an amount in the range of, for example, 0.5 to 2 degrees) to obtain the IVUS signal from the next region. By rotating completely around a circle in this manner, a 360° IVUS image can be generated. Each position of the transducer produces an IVUS signal which is may be referred to as a "scan line". The ongoing rotation of the transducer allows the generation of "real-time" IVUS images. In at least some embodiments, the IVUS transducer rotates at least one, twice, three times, five times, ten times, twenty times, or thirty times per second. Other rotation rates may also be used.

If the tissue region extends over multiple scan lines, the frequency spectrum for any particular tissue region can be obtained from an average of a windowed section of the IVUS signal over two or more scan lines (e.g., over one, two, three, four, five, six, seven, eight, nine, or ten scan lines). The frequency spectrum may also be computed from an average of two or more (e.g., two, four, 10, 16, 25, 32, 50, 64, 100, 128, or more) samples of each scan line. Either the IVUS signals or the corresponding frequency spectra can be averaged. In some instances, the average may be a weighted average of the individual spectra, particularly if the tissue region of interest only overlaps a portion of the region represented by a particular scan line.

Figures 1A, 1B, 1C, 1D, 2:
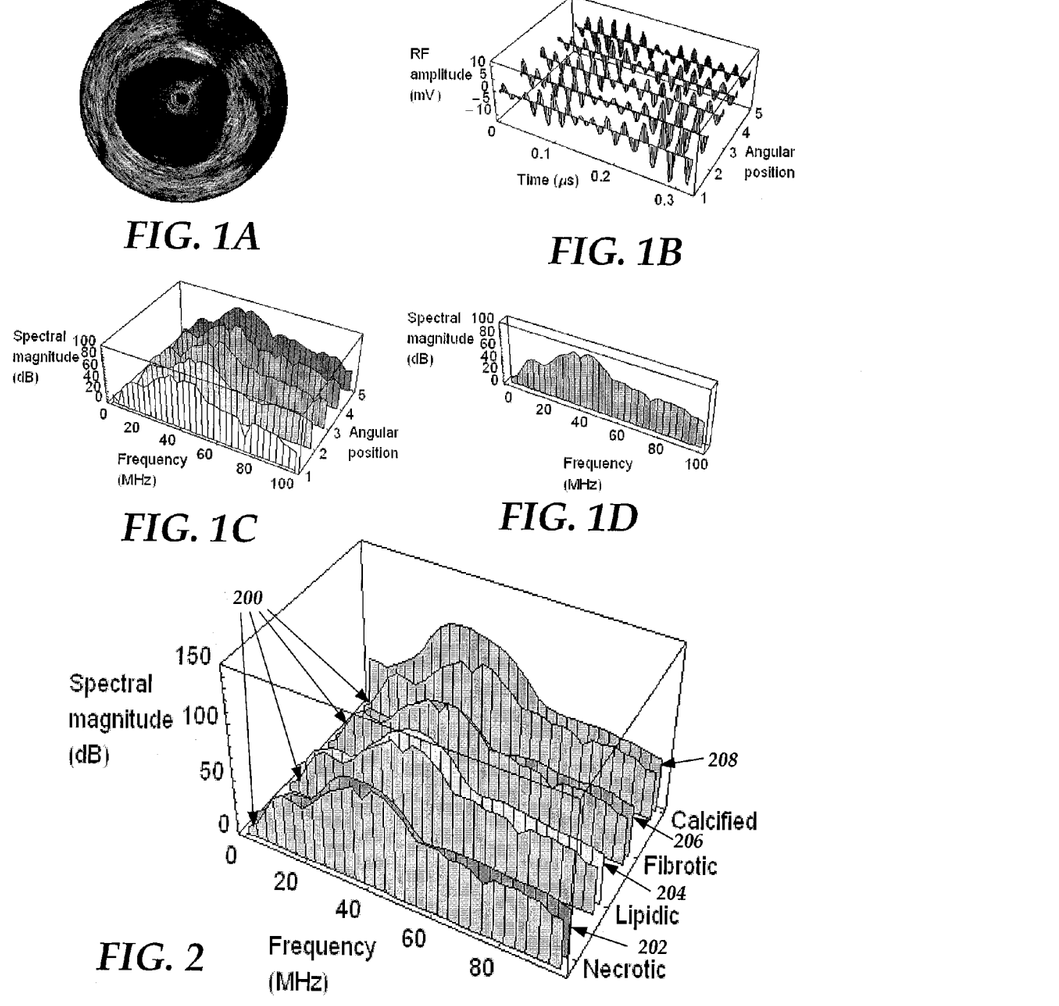
FIG. 1A is an IVUS image illustrating, within a small box, a tissue region of interest.
FIG. 1B is a schematic graphical representation of the raw IVUS signal for five adjacent scan lines for the tissue region in FIG. 1A.
FIG. 1C is a schematic graphical representation of the frequency spectra of the five IVUS signals of FIG. 1B.
FIG. 1D is a schematic representation of an averaged frequency spectrum of the five spectra of FIG. 1C.
FIG. 2 is a schematic graphical representation of comparisons between an input spectrum and four tissue-type assigned spectra (input spectrum is positioned in front of each tissue-type assigned spectrum), according to the invention.

As an example, FIG. 1A illustrates an IVUS image with a particular tissue region indicated by the small box on the image. FIG. 1B schematically illustrates the IVUS signal for the particular tissue region which is covered by five scan lines. FIG. 1C schematically illustrates the spectra calculated for these five scan lines at this tissue location. FIG. 1C schematically illustrates an average of the five spectra.

The entire frequency spectrum of a sample region, or only a portion of the frequency spectrum, can be used as the input spectrum for the tissue classifier. The frequency spectrum may include any suitable range of frequencies. In one embodiment, the range of frequencies is 0 to 100 MHz or 0 to 60 MHz or 0 to 80 MHz or 20 to 60 MHz. Preferably, the tissue characterization uses the entire usable frequency spectrum, for example, from 0 to 100 MHz. While this approach may involve more mathematical calculations than algorithms using reduced or summarized data/spectra, it typically increases the chances of correctly recognizing tissue type by avoiding discarding any potentially useful information.

The input spectrum is used to infer tissue type on the basis of spectral similarity to a library of spectra corresponding to known tissue types (i.e., tissue type-assigned spectra) using the structure of the tissue classifier. A comparison can be performed using any known method of assessing spectral similarity. For example, the concept of Euclidean distance can be used to mathematically define a measure of similarity between the input spectrum and a tissue type-assigned spectrum. For example, the amount of overlap of between the two spectra or the amount of non-overlap of the two spectra can be used to define spectral similarity. Other methods for assessing spectral similarity include, for example, the average absolute difference in spectral energy at one or more preselected frequencies. FIG. 2 schematically illustrates a comparison of an input spectrum 200 (copied four times) with a necrotic tissue spectrum 202, lipidic tissue spectrum 204, calcified tissue spectrum 206, and fibrotic tissue spectrum 208. In this example, the input spectrum is seen to be most similar to the fibrotic tissue spectrum.

Generally, the comparison of an input spectrum with only one spectrum for each type of tissue is not sufficiently robust to provide confidence in accurate tissue classification. Accordingly, a tissue classifier can be developed that includes arrays of tissue detectors and a combiner that combines the results of the detector arrays to generate a characterization output and, optionally, a confidence level for that tissue characterization.

Figure 3:
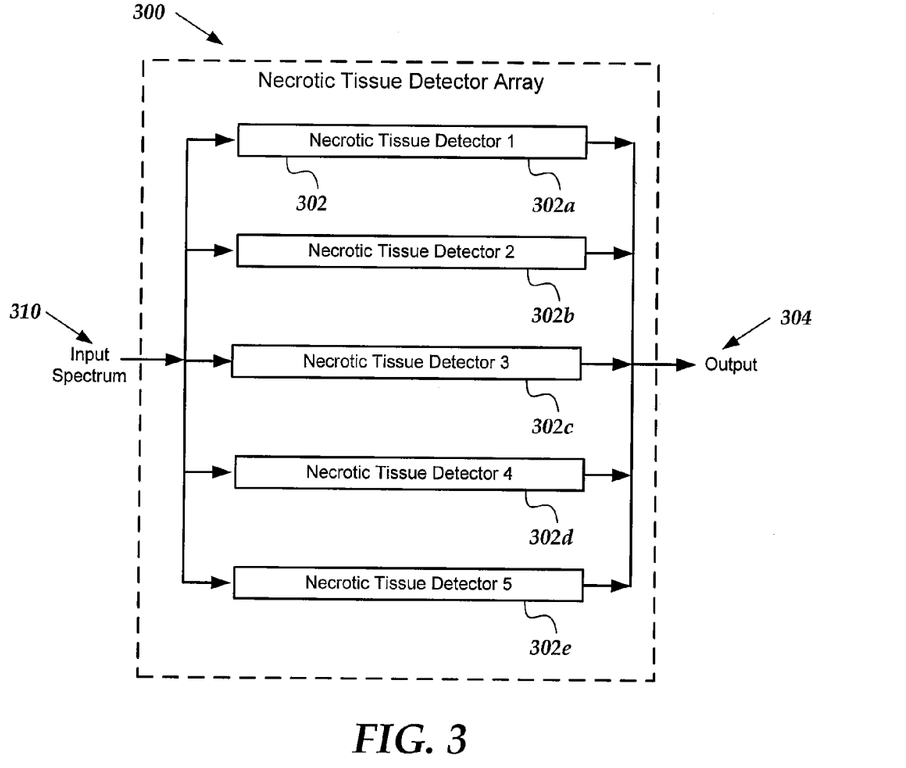
FIG. 3 is a schematic diagram of one embodiment of a tissue detector array, according to the invention.

FIG. 3 is a schematic diagram of one detector array 300 of a tissue classifier. Each detector array 300 is arranged to provide an output indicative of whether, based on the output of detectors in the array, the input spectrum 310 belongs to a particular tissue type or not. In the example illustrated in FIG. 3, the detector array 300 is arranged to provide an output indicative of whether, based on the output of detectors in the array, the input spectrum corresponds to necrotic tissue or not.

The detector array 300 includes multiple detectors 302 (detectors 302a, 302b, 302c, 302d, and 302e). The detectors are specifically tuned to the particular tissue type associated with the detector array. For example, the detector 302a is labeled "Necrotic Tissue Detector #1" because it is designed to test whether, based on spectra of the detector, the input spectrum represents necrotic tissue or not. The detector array 300 may include any number of detectors. For example, a detector array may include two, three, four, five, six, seven, eight, nine, or ten detectors. Moreover, each detector array in the tissue classifier can have the same number of detectors or detector arrays in the tissue classifier may have different numbers of detectors.

Each detector contains a library of spectra corresponding to the tissue type of the detector and to other tissue types. For example, detector 302 includes spectra corresponding to necrotic and non-necrotic tissue. The detector 302 has the ability to perform spectral similarity comparisons between the input spectrum and each of the library spectra. A detector will typically include multiple spectra corresponding to the tissue type of the detector and multiple spectra corresponding to other tissue types. Preferably, the detector includes samples of each type of tissue in the classification.

A detector may have any number of spectra in its library. For example, the library may include three, four, five, six, seven, eight, ten, 12, 16, 20, 24, 32, or more spectra. Each detector may have the same number of spectra or the number of spectra for detectors can be different. Spectra may also be identified as belonging to saline-filled vessels or tissue or blood-filled vessels or tissue and the detector, array, or classifier (or any combination thereof) may account for variations due to saline and blood.

By determining the spectral similarity between the input spectrum and the spectra in the library of the detector 302, the detector provides an output regarding whether, based on the spectra of the library, the input spectrum is likely to correspond to the tissue type of the detector or not. As indicated above, any method for determining spectral similarity can be used. In at least some embodiments, the detector may determine whether the input spectrum is more similar to one or more of the spectra corresponding to the tissue type of the detector or more similar to one or more of the spectra of the other tissue types. In some embodiments, the output of a detector can be a binary output (e.g., +1, if the detector determines that the input spectrum corresponds to the tissue type of the detector; −1, otherwise). In other embodiments, the output of the detector can be a numerical output indicating the likelihood that the input spectrum corresponds to the tissue type of the detector.

The outputs of the detectors 302 of the detector array 300 are then combined to provide an array output 304. The outputs of the detectors 302 can be combined with or without weighting those outputs. In at least some embodiments, the outputs of the detectors 302 may be individually weighted. In at least one embodiment, a weighted combination of the five outputs of the five detectors 302 in FIG. 3 can be arranged (e.g., trained) so that it rises above zero when the detector array 300 is presented with a spectrum from necrotic tissue and falls below zero when presented with a spectrum from one of the other types. In at least some embodiments, the output of an array is not a binary number even if the outputs of the individual detectors were binary.

Any suitable method for determining the weights can be used. In one embodiment, the weights for the detectors can be determined by using the classifier, individual arrays, or individual detectors to characterize spectra of known tissue type. This is one method of training the classifier, array, or detector. For example, the weighting of each detector 302 can be based on the accuracy with which the detector determines whether the known spectra (i.e., "training spectra") belong to the tissue type of the detector or not. Other methods of determining weights can be used including general mathematical optimization techniques.

Figure 4:
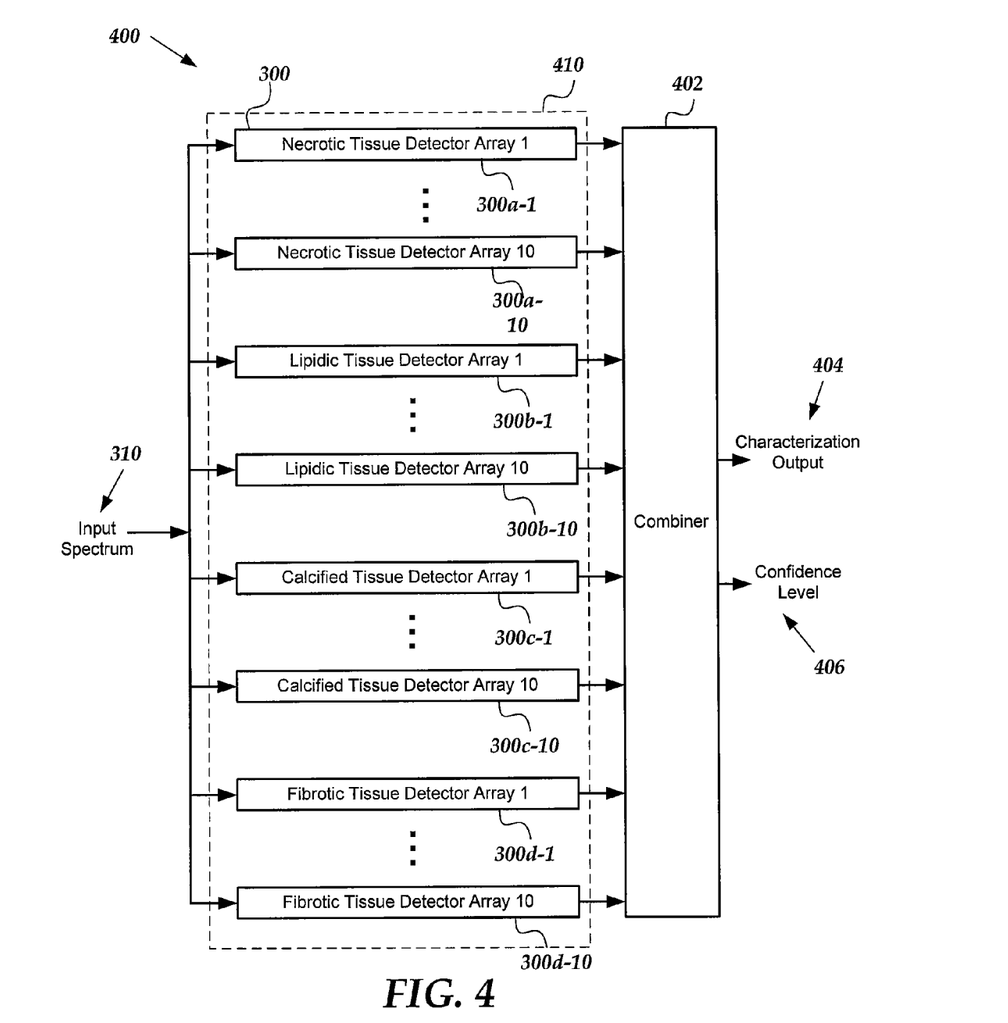
FIG. 4 is a schematic diagram of one embodiment of a tissue classifier, according to the invention.

A tissue classifier includes multiple detector arrays for each tissue type. The number of detector arrays for each tissue type can be the same or can be different. It is often advantageous to design a tissue classifier with several arrays for each tissue type by letting each array be built utilizing randomly selected subsets of spectra. FIG. 4 schematically illustrates a tissue classifier 400 with a bank 410 of detector arrays including arrays for each of four tissue types: necrotic tissue detector arrays 302*a*-1 to 302*a*-10, lipidic tissue detector arrays 302*b*-1 to 302*b*-10, calcified tissue detector arrays 302*c*-1 to 302*c*-10, and fibrotic tissue detector arrays 302*d*-1 to 302*d*-10. Any number of detector arrays can be used. In FIG. 4, the illustrated embodiment of the tissue classifier 400 includes 40 detector arrays arranged in four groups of ten. Essentially, the bank 410 of detector arrays takes an input spectrum 310 and processes it to yield a set of 40 outputs. As an example, when presented with an input spectrum from lipidic tissue, the bank 410 of detector arrays of the tissue classifier 400 preferably produces an output in which elements 11 through 20 are stronger than the others.

The classifier 400 includes a combiner 402 that takes the outputs of the bank 410 of detector arrays and makes a final characterization 404 of tissue type based on those outputs. Any method of characterizing the tissue type from the outputs of the detector arrays can be used. In one embodiment, the combiner 402 can accomplish the characterization by checking which of the numbers in the set are positive and which are negative (assuming that positive outputs indicate that the tissue is of the tissue type of the detector array and negative outputs indicate that the tissue is not of the tissue type of the detector array). In another embodiment, the combiner 402 uses a Bayesian-type classifier. Other types of classifiers include, but are not limited to, simple majority voting and Fisher's Linear Discriminant. The combiner 402 may also individually weight the outputs of the detector arrays. The individual weights may be based, for example, on training of the tissue classifier using spectra of known tissue type as the input spectrum.

In addition to characterizing the tissue, the combiner 402 optionally also determines a measure of the level of confidence in that characterization. A confidence level 406 can be computed using any suitable method. In one embodiment, the confidence level is computed within the combiner 402 by comparing a degree of similarity between the outputs from the bank of detector arrays and ideal expected patterns corresponding to the recognized tissue type or patterns identified during training with spectra of known tissue type.

Accordingly, the methods, devices, and systems disclosed herein can not only classify tissue into categories but they may also provide a measure of the confidence in the characterization of each region of interest, if desired. As an example, the confidence level feature may distinguish between the characterization of two regions both being recognized as lipidic—but with one region whose spectral properties make it slightly closer to lipidic than necrotic (and, therefore, the confidence level in the tissue characterization would be expected to be lower), and another region whose spectral properties are clearly those of lipidic tissue (with an expectation of a relatively high level of confidence in the tissue characterization). In one embodiment, the system adjusts the transparency, or other characteristic, of color on the characterized image according to the confidence level.

The tissue characterization 404 can be presented to a practitioner or other viewer in any suitable manner, including numerically, graphically, or using one or more images. In one embodiment, tissue type can be presented in conjunction with an IVUS image by coloring regions of the IVUS image (or presenting a colored representation next to an IVUS image) based on the tissue characterization. For example, each type of tissue could be represented by a different color, gray-scale shade, or pattern. A legend can also be presented with the image to indicate the colors, shades, or patterns corresponding to the tissue types.

Optionally, the confidence level can also be represented by varying a characteristic of the colored portion. Examples of characteristics that can be varied include transparency, brightness, hue, color, shade, texturing, and the like. As an example, regions with a higher confidence level for the tissue characterization can be shown with more solid color.

Figure 5:
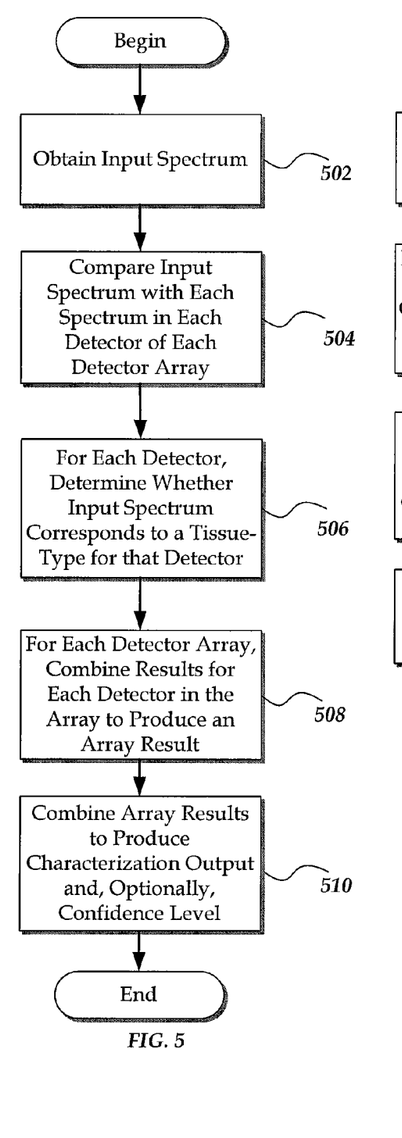
FIG. 5 is a flow-chart of one embodiment of a method of characterizing tissue, according to the invention.

As an example of the characterizing tissue, one embodiment of a method using the tissue classifier described above is illustrated in the flow chart of FIG. 5. An input spectrum is obtained (step 502). The input spectrum is compared with each spectrum in the library of each detector of each detector array of a tissue classifier (step 504). It will be recognized that, in some embodiments, a subset of detectors or a subset of detector arrays may be used by the tissue classifier. The comparison can include, for example, comparing the spectral similarity between the input spectrum and library spectra of the tissue detector. Each detector then provides an output indicating whether, based on the comparisons with the detector spectra, the input spectrum corresponds to the tissue type for the detector or not (Step 506). The output of each of the detectors in a detector array is combined to provide an array result (step 508). This combination may be weighted or unweighted for each detector. The array results are then combined to produce a tissue characterization output and, optionally, a confidence level in the characterization (step 510). Again, the array results can be weighted or unweighted.

Figure 6:
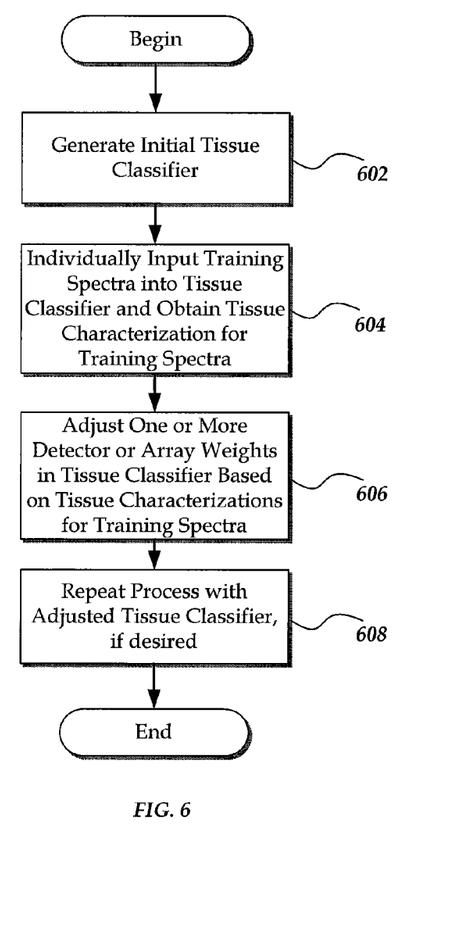
FIG. 6 is a flow-chart of one embodiment of a method of training a tissue classifier, according to the invention.

The flow chart of FIG. 6 illustrates one embodiment of a method of training a tissue classifier using spectra of known tissue type. First, a tissue classifier, with arrays and detectors as described above, is generated using a library of spectra (step 602). Alternatively, a previously generated (or even trained) tissue classifier can be used. Next, training spectra are individually input into the tissue classifier and a tissue characterization is obtained (step 604). The training spectra are typically spectra of a known tissue type. After obtaining the tissue characterizations of one or more training spectra, the weights of one or more detectors or arrays can be adjusted based on the tissue characterization(s) (step 606). This process can be repeated, as desired, with more training spectra and using the adjusted tissue classifier (step 608).

This approach characterizes the tissue type in a direct way by comparing the spectrum from an area on a vessel to entries in a library of spectra corresponding to known tissue types. By comparing spectra directly, tissue type is not inferred using secondary derived features whose discriminating properties have not been established. This approach can also employ an extensive library of spectra which includes data acquired from vessels filled with blood in addition to those more conventionally obtained from saline-filled vessels. The spectrum altering properties of blood are generally well-known and the method can take this into account so that the tissue characterization system calibrated using in vitro data will work correctly in vivo.

The tissue classifier disclosed herein may include one or more features intended to enhance tissue characterization. For example, the tissue classifier may combine the directness and accuracy of similarity-based methods with the ability of model-based methods to understand the training data (i.e., spectra of known tissue type used to test the system or determine weights for detectors or detector arrays) to classify new data. Having a large and diverse collection of independently designed classifiers can produce a more accurate classifier. It will be understood that the methods, devices, systems, and tissue classifiers disclosed herein can be useful in characterizing tissue using other (non-ultrasound) data including spectra or other data obtained using other imaging techniques. In particular, the methods and classifiers can be used to distinguish between subtly different object types whose difference in properties is not easily quantifiable The development of a reliable and accurate tissue characterization system can be useful in a variety of diagnostic and treatment settings. For example, tissue characterization can be used to study plaques.

Plaque rupture is the most common type of plaque complication, accounting for around 70% of fatal acute myocardial infarctions and/or sudden coronary deaths. The goal of treatment of coronary arterial disease is the prevention of acute coronary syndrome. Intravascular ultrasound (IVUS) is commonly used in conjunction with angiography as an assessment tool to guide treatment of coronary arterial disease. IVUS images, in their traditional grayscale form, significantly add to diagnostic information provided by angiography especially in determining coronary vessel dimensions and borders of plaques. Research initiatives in tissue characterization seek to develop methods that complement the information provided by IVUS in assessing the composition of plaques such as fibrofatty tissue, necrotic tissue and various stages of thrombus. For example, there would be clinical value in developing a method to distinguish between loose fibrous plaques classified as American Heart Association (AHA) type II or III and atheroma with a lipid core classified as AHA type IV or Va.

Tissue classification, using the methods and tissue classifier disclosed herein, can be useful to classify plaques with the highest probability of spontaneous rupture. The information obtained from tissue characterization in combination with an understanding of the natural history of coronary artery disease may translate into a meaningful treatment protocol that decreases patient morbidity and mortality.

In addition to classifying tissue, the size of a particular tissue type or the amount of a particular tissue type in a selected portion or portions of a particular image or set of images can be determined. This quantitative output can provide specific and numerical information that may be of clinical benefit. The size or amount may be provided (e.g., on a display of a computer system or printed on paper or other medium) in relative terms (e.g., as a percentages or fraction of total size or amount of a particular selected portion or portions) or in absolute terms (e.g., in $mm^2$ or $mm^3$) or both.

Figure 9:
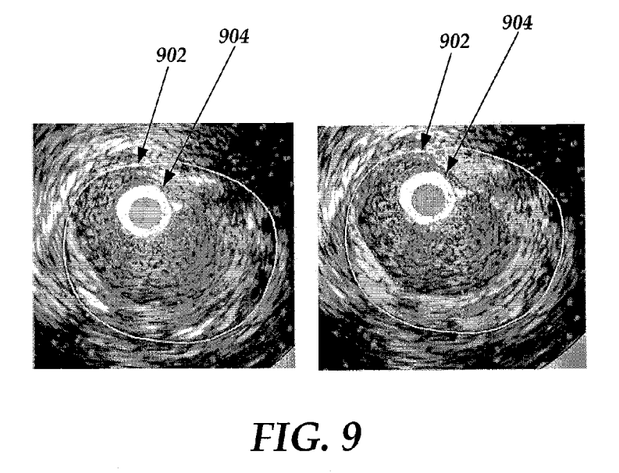
FIG. 9 is a schematic representation of two versions of the same IVUS image with boundaries marked on the left image and classified tissue types indicated on the right image.

Returning to FIG. 9, the system or a user can determine boundaries of the image portion or portions to be classified. In some embodiments, the system may suggest boundaries and the user may accept the suggested boundaries or modify the boundaries. In the example illustrated in FIG. 9, there is an outer boundary 902 and an inner boundary 904 with the selected portion for classification between these two boundaries. It will be understood that in at least some embodiments any portion or portions can be selected on the image and that there may be any suitable number of boundaries to demark the selected portion or portions.

In at least some embodiments, after classification of the tissue in the selected portion or portions of one or more images, a relative amount of one or more of the tissue types within the selected portion or portions can be determined. For example, the relative amount of a particular tissue type can be determined as the percentage of individual regions (each region being associated with a particular input spectrum) within the selected portion or portions that have been classified as the particular tissue type. This relative amount of the particular tissue type may be displayed as a percentage or in any other suitable format. In some embodiments, the relative amounts of each of the particular tissue types (or more than one of the tissue types) may be displayed. Moreover, the confidence level in the relative amount of a particular tissue type can be determined using the confidence levels in the individual classification of the regions.

Figure 10:
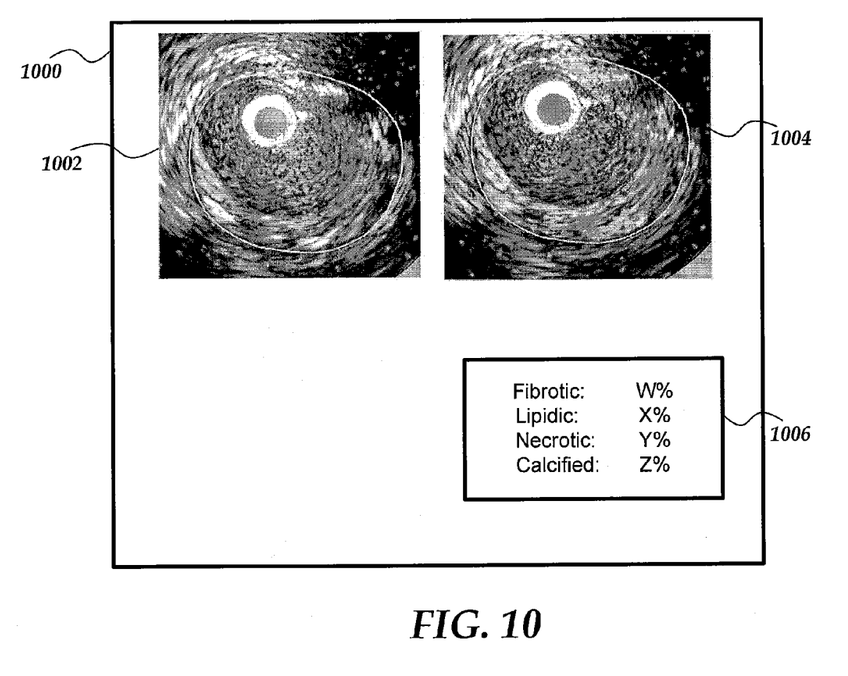
FIG. 10 is schematic representation of one embodiment of a display of two versions of the same IVUS image and information about the amount of each tissue type in a selected portion of the image.

FIG. 10 schematically illustrates one example of a display 1000. The display includes an IVUS image 1002 with the boundaries demarked, as well as an IVUS 1004 image with color-coded classification of the tissue in the selected portion demarked by the boundaries. The display also includes a section 1006 which reports the percentage of each type of tissue in the selected portion. It will be understood that the display of FIG. 10 is merely one example of how this information can be displayed.

In some embodiments, a size (e.g., in $mm^2$ or $mm^3$ or other appropriate units) of the particular tissue type in the selected portion or portions can be determined and displayed (e.g., in section 1006 of FIG. 10), if desired. For example, an area in $mm^2$ or volume in $mm^3$ (or other appropriate units) can be assigned to the size of the region associated with each input spectrum in the classification process (e.g., each region that is classified). Preferably, each region will be assigned the same area or volume. The total size of the particular tissue type is then a combination of the area/volume associated with each region classified with that tissue type. Moreover, the confidence level in the area or volume of a particular tissue type can be determined using the confidence levels in the individual classification of the regions.

Volume of the particular tissue type in the selected portion or portions can also be determined by determining the area of the tissue type in several images taken along a vascular lumen. For example, the images may be consecutive images obtained during a pullback procedure, although non-consecutive images may also be used. The volume can then be calculated using these areas and the distances between the images. For example, the volume might be the summation, over the set of images, of the product of the area of tissue type and the distance to the next image (or the average of the distance to the immediately preceding and immediately succeeding images). Alternatively, extrapolation techniques may be used to extrapolate changes in area between images to determine the volume.

In at least some embodiments, a system may be configured and arranged to allow a user to select a portion of an image or images after tissue classification and then the area or volume or both of a particular tissue type can be determined for the selected portion or portions. For example, a user may select a portion of an image or images that contains fibrous plaque to determine the size (e.g., area or volume or both) of the plaque.

In at least some embodiments, one or more display choices may be available. For example, a user may have the option to select which tissue types to display as colored regions and for which tissues types amount or size will be determined or displayed. The user may have an option to select from a choice of measurements to display such as relative area or volume (e.g., in percent), absolute area (e.g., in $mm^2$), or absolute volume (e.g., in $mm^3$). Alternatively or additionally, icons or labels (e.g., mild, moderate, or severe) may be used in place of, or in addition to, numbers of the amount or size. It will be understood that the determination of amount or size of a tissue type and the display thereof can be applied to tissue characterization as determined by any suitable method including, but not limited to, the methods for tissue characterization described herein.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,306,561 and 6,945,938; as well as U.S. Patent Application Publication Nos. 20060253028; 20070016054; 20070038111; 20060173350; and 20060100522, all of which are incorporated by reference.

Figure 7:
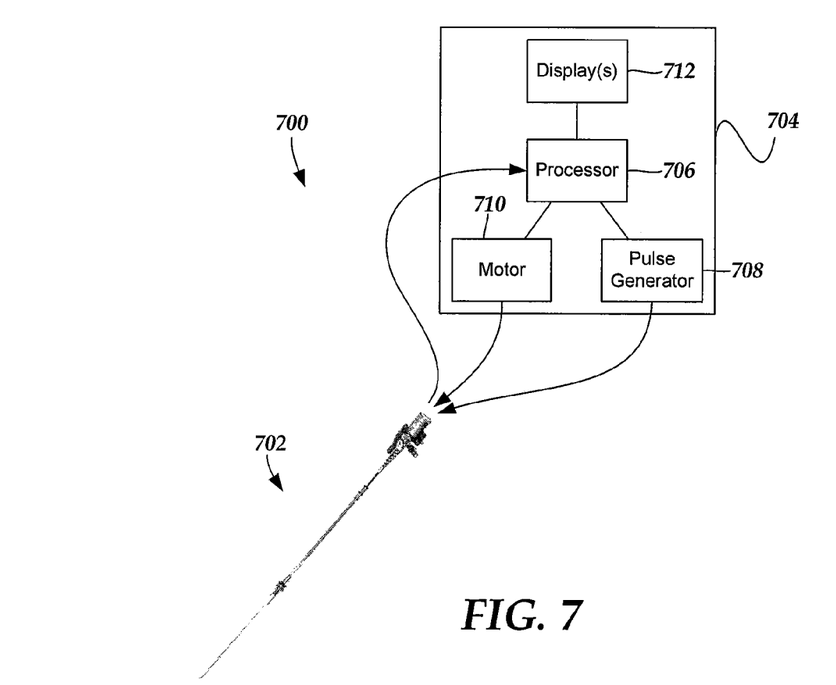
FIG. 7 is a schematic representation of an IVUS imaging system, according to the invention.

FIG. 7 illustrates schematically one embodiment of an IVUS imaging system 700. The IVUS imaging system 700 includes a catheter 702 that is coupleable to a control module 704. The control module 704 may include, for example, a processor 706, a pulse generator 708, a motor 710, and one or more displays 712. In at least some embodiments, the pulse generator 708 forms electric pulses that may be input to one or more transducers disposed in the catheter 702. In at least some embodiments, mechanical energy from the motor 710 may be used to drive an imaging core disposed in the catheter 702. In at least some embodiments, electric pulses transmitted from the one or more transducers may be input to the processor 706 for processing. The processor 706 may also include a tissue classifier as described herein. Alternatively or additionally, the tissue classifier may be provided with any suitable processor including, but not limited to, a computer that is connected to, or separate from, the IVUS imaging system.

The tissue classifier, systems, and methods described herein may be embodied in many different forms and may be embodied as methods, systems, or devices. Accordingly, the tissue classifier, detector arrays, detectors, systems, and methods disclosed herein may take the form of an entirely hardware embodiment, an entirely software embodiment or an embodiment combining software and hardware aspects.

It will be understood that each block of the flowchart illustrations, and combinations of blocks in the flowchart illustrations, as well any portion of the tissue classifier, detector arrays, detectors, systems and methods disclosed herein, can be implemented by computer program instructions. These program instructions may be provided to a processor to produce a machine, such that the instructions, which execute on the processor, create means for implementing the actions specified in the flowchart block or blocks or described for the tissue classifier, detector arrays, detectors, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

EXAMPLES

Example 1

Ex Vivo Human Data Collection

IVUS AND HISTOLOGY: Atlantis SR PRO 40 MHz single-element mechanically rotating catheters (Boston Scientific Corp, Fremont, Calif.) were used to acquire cross-sectional ultrasound images of excised human arteries at a pullback speed of 0.5 mm/s and a frame rate of 30 frames per second. The data was from twenty five hearts that were obtained within twenty four hours of autopsy. After being dissected and mounted in a tissue fixture filled with phosphate buffered saline (PBS) at physiologic pressure, the arteries were imaged from distal end to proximal end by an automatic catheter pullback procedure. This procedure was repeated with human blood circulating within the lumen at physiologic pressure. The RF data were digitized using a two-board 12-bit Acqiris system [Monroe, N.Y.] at a sampling rate of 400 MHz. The RF data was cataloged and stored for subsequent analysis. The vessel tissue samples were then fixed in formalin and sections for histological analysis were prepared every 2 mm using standard laboratory techniques. The sections were stained with Hemtoxylin & Eosin, and Movat Pentachrome to delineate areas of collagen, calcifications, and lipid.

The available data amounted to 120 cross sections representing left anterior descending, left circumflex, and right coronary arteries of which 75 cross sections were imaged through saline and 45 cross sections were imaged through blood. Care was taken to use a number of different catheters in order to add variation in the data.

Example 2

In Vivo Animal Data Collection

DIABETES-INDUCED ATHEROSCLEROSIS A porcine model involving the administration of streptozotocin in conjunction with a diet high in fat and cholesterol was used to induce atherosclerosis. The protocol was approved by Harvard's Institutional Animal Care and Use Committee.

IVUS AND HISTOLOGY Once plaque formation was established, pullback data was acquired as described above in Example 1. Coronary arteries from the pigs were harvested and preserved at −80° C. The arteries were frozen cut at the middle of the subsegments of interest and cryosectioned (7 μm sections). Verhoeff's elastin-stained cryosections were stained with oil red O solution. Infiltration of inflammatory cells into intima was assessed by immunostaining using monoclonal antibody (clone 2A5, BD Biosciences Inc., San Jose, Calif.) against pig CD45 leukocyte common antigen. Picrosirius red staining was applied to detect collagen types I and III. Olympus BX41 microscope with an Olympus DP70 digital camera was used for the digitization of oil red O- and CD45-stained sections, whereas picrosirius red sections were digitized by polarization microscopy (Nikon-Optiphot-2 microscope with Nikon polarizer lenses and Sony DFW-SX900 digital camera).

Example 3

Ex Vivo Validation

As described above, the local spectrum of the radiofrequency signal corresponding to a location on the IVUS image was used as the predictor of tissue type. The local spectrum was computed by averaging the magnitude of the windowed spectrum from 128 RF samples over 5 adjacent A-lines (see, FIGS. 1A-1D). These regions-of-interest (ROIs) were uniformly distributed over all plaque regions that could be identified. The first 32 frequency bins representing a range of frequencies from 0 to 100 MHz were retained. The last element of the spectra was replaced with a 0 for saline or 1 for blood. A set of about 12000 spectra along with their known tissue type labels (classes) were available for classifier design and accuracy assessment. This set was randomly partitioned into a training set and a testing set containing 75% and 25% of the predictors, respectively. The number of training and testing predictors grouped by tissue type and lumen medium is given in Table 1.

TABLE 1

|  | Training | | Testing | |
| --- | --- | --- | --- | --- |
|  | Saline | Blood | Saline | Blood |
| Necrotic | 626 | 350 | 208 | 116 |
| Lipidic | 542 | 322 | 180 | 108 |
| Fibrotic | 3458 | 1588 | 1152 | 530 |
| Calcified | 1063 | 1143 | 354 | 381 |

Validation of the spectral similarity algorithm was performed using a five-step process:
 1. Mean spectra were computed for ROIs of histologically determined type
 2. The spectra were randomly partitioned into test and training sets: 75% of the spectra were used for training the spectral similarity algorithm and the remaining 25% were used as the test set
 3. The spectral similarity algorithm was then used to classify the test set
 4. Steps 2 and 3 were repeated four times to reduce possible bias from the test set selection
 5. The accuracy of the algorithm was computed by comparing the characterization of each sub-region against the known histological tissue type.

Figure 8:
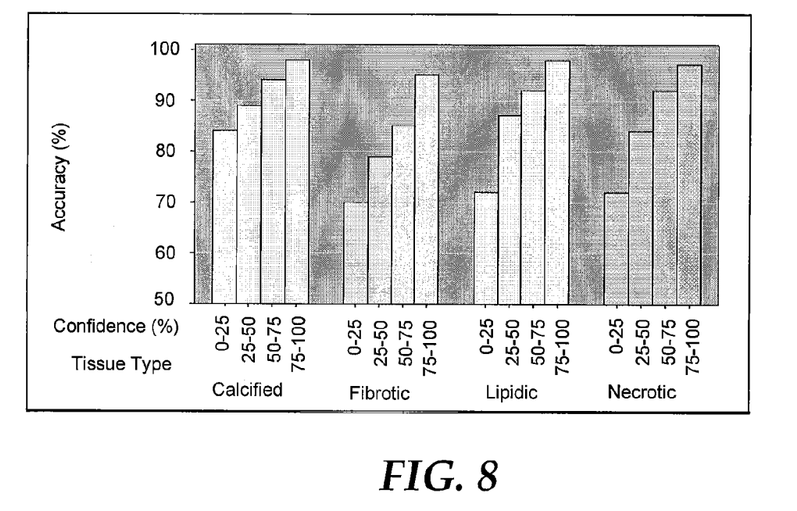
FIG. 8 is a bar graph of accuracy percentage versus confidence level for each tissue type, the bar graph was generated using ex vivo human tissue samples and the methods described herein and showing that for tissue regions characterized with the highest confidence (75-100%) the accuracy ranges from 95% to 98%.

FIG. 8 shows an example of ex vivo tissue characterization of human coronary artery infused with blood. The accuracy of the similarity algorithm in characterizing each of the four tissue types is shown grouped by confidence measure. For tissue regions characterized with the highest confidence (75-100%) the accuracy ranges from 95% to 98%. Even at the lowest confidence (0 to 25%) the accuracy is above 70%. The accuracy increases monotonically with confidence, confirming that the confidence measure computed by the algorithm may provide an estimate of the probable accuracy of the classification on a pixel-by-pixel basis.

To locate the correct cutting points, two to three major readily visible side branches were identified on the IVUS pullbacks and used as references for the determination of the location of the cross sections of interest. The same branches were also identified on the harvested arteries, by visual inspection. These branches were used as landmarks to correlate histology images and their corresponding IVUS counterparts.

The IVUS and histology images were examined side-by-side and regions corresponding to necrotic, lipidic, calcified, and fibrotic tissue were marked on the IVUS image using image editing tools. A color-coded tissue map was then generated with the various tissue types labeled in specific colors. A comparison between a histological sample and the tissue classifications determined using the above-described methods showed good correlation.

Example 4

In Vivo Animal Study

Using the animal data available, qualitatively verification of the correctness of the predicted tissue types was made. A comparison between a histological sample and the tissue classifications determined using the above-described methods showed good correlation.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of evaluating at least one tissue type in at least one intravascular ultrasound (IVUS) image, the method comprising:
 a) providing a tissue classifier comprising a plurality of detector arrays for each of a plurality of tissue types, wherein each detector array comprises a plurality of detectors and each detector comprises a plurality of tissue type-assigned IVUS spectra, wherein a plurality of the tissue type-assigned IVUS spectra of each detector correspond to a tissue type of the detector and a plurality of tissue type-assigned IVUS spectra correspond to other tissue types;
 b) comparing an input IVUS spectrum of a region in the at least one intravascular ultrasound image to the tissue type-assigned IVUS spectra of each of the plurality of detectors for each of the plurality of detector arrays;
 c) determining, for each of the plurality of detectors of each of the plurality of detector arrays, whether the input IVUS spectrum corresponds to the tissue type of the detector based on the comparisons of the input IVUS spectrum to the tissue type-assigned IVUS spectra for that detector;

d) for each of the plurality of detector arrays, combining results of the plurality of detectors of the detector array to produce an array result;

e) combining the array results for the plurality of detector arrays to provide a tissue characterization of the region from the plurality of tissue types;

f) repeating b) to e) for each region to be characterized in the at least one intravascular ultrasound image;

g) determining a size of at least one of the tissue types in a selected portion of the at least one intravascular ultrasound image using the tissue characterizations of the regions in the selected portion; and h) displaying one or more of the at least one intravascular ultrasound image with an indication of the tissue characterization of one or more regions of the at least one intravascular ultrasound image that is displayed and an indication of the size of at least one of the tissue types in the selected portion of the at least one intravascular ultrasound image that is displayed.

2. The method of claim 1, wherein determining the size of at least one of the tissue types comprises determining the size of each of the tissue types in a selected portion of the at least one intravascular ultrasound image using the tissue characterizations of the regions in the selected portion.

3. The method of claim 2, wherein displaying one or more of the at least one intravascular ultrasound image comprises displaying one or more of the at least one intravascular ultrasound image with an indication of the tissue characterization of one or more regions of the at least one intravascular ultrasound image that is displayed and an indication of the size of each of the tissue types in the selected portion of the at least one intravascular ultrasound image that is displayed.

4. The method of claim 1, wherein determining the size of at least one of the tissue types comprises determining a relative size of at least one of the tissue types in a selected portion of the at least one intravascular ultrasound image using the tissue characterizations of the regions in the selected portion.

5. The method of claim 1, wherein determining the size of at least one of the tissue types comprises determining an absolute area of at least one of the tissue types in a selected portion of the at least one intravascular ultrasound image using the tissue characterizations of the regions in the selected portion.

6. The method of claim 1, wherein step f) is repeating b) to e) for each region to be characterized in a plurality of intravascular ultrasound images; and
wherein determining the size of at least one of the tissue types comprises determining an absolute volume of at least one of the tissue types in a selected portion of the at least one intravascular ultrasound image using the tissue characterizations of the regions in the selected portion.

7. The method of claim 1, further comprising combining the array results for the plurality of detector arrays to provide a confidence level associated with the tissue characterization for each region characterized in the at least one intravascular ultrasound image.

8. The method of claim 7, further comprising using the confidence levels associated with the tissue characterization for each region characterized in the at least one intravascular ultrasound image to determine a confidence level in the determined size of at least one of the tissue types in a selected portion of the at least one intravascular ultrasound image.

9. The method of claim 1, wherein displaying one or more of the at least one intravascular ultrasound image with an indication of the tissue characterization of one or more regions of the at least one intravascular ultrasound image comprises coloring each characterized region on the at least one intravascular ultrasound image with a color assigned to a tissue type corresponding to the tissue characterization.

10. The method of claim 9, further comprising reflecting a confidence level associated with the tissue characterization by-varying a display characteristic of the coloring of each characterized region according to the confidence level.

11. The method of claim 10, wherein the display characteristic is selected from transparency, brightness, hue, color, shade, and texture.

12. A non-transitory computer-readable medium having processor-executable instructions for characterizing tissue, the processor-executable instructions when installed onto a device enable the device to perform actions, comprising:

a) providing a tissue classifier comprising a plurality of detector arrays for each of a plurality of tissue types, wherein each detector array comprises a plurality of detectors and each detector comprises a plurality of tissue type-assigned IVUS spectra, wherein a plurality of the tissue type-assigned IVUS spectra of each detector correspond to a tissue type of the detector and a plurality of the tissue type-assigned IVUS spectra correspond to other tissue types;

b) comparing an input IVUS spectrum of a region in the at least one intravascular ultrasound image to the tissue type-assigned IVUS spectra of each of the plurality of detectors for each of the plurality of detector arrays;

c) determining, for each of the plurality of detectors of each of the plurality of detector arrays, whether the input IVUS spectrum corresponds to the tissue type of the detector based on the comparisons of the input IVUS spectrum to the tissue type-assigned IVUS spectra for that detector;

d) for each of the plurality of detector arrays, combining results of the plurality of detectors of the detector array to produce an array result;

e) combining the array results for the plurality of detector arrays to provide a tissue characterization of the region from the plurality of tissue types;

f) repeating b) to e) for each region to be characterized in the at least one intravascular ultrasound image;

g) determining a size of at least one of the tissue types in a selected portion of the at least one intravascular ultrasound image using the tissue characterizations of the regions in the selected portion; and h) displaying one or more of the at least one intravascular ultrasound image with an indication of the tissue characterization of one or more regions of the at least one intravascular ultrasound image that is displayed and an indication of the size of at least one of the tissue types in the selected portion of the at least one intravascular ultrasound image that is displayed.

13. The computer-readable medium of claim 12, wherein the actions further comprise reflecting a confidence level associated with the tissue characterization by selecting a display characteristic of the coloring of the tissue region.

14. The computer-readable medium of claim 12, wherein determining the size of at least one of the tissue types comprises determining the size of each of the tissue types in a selected portion of the at least one intravascular ultrasound image using the tissue characterizations of the regions in the selected portion.

15. The computer-readable medium of claim 12, wherein determining the size of at least one of the tissue types comprises determining a relative size of at least one of the tissue types in a selected portion of the at least one intravascular ultrasound image using the tissue characterizations of the regions in the selected portion.

16. The computer-readable medium of claim 12, wherein determining the size of at least one of the tissue types comprises determining an absolute area of at least one of the tissue types in a selected portion of the at least one intravascular ultrasound image using the tissue characterizations of the regions in the selected portion.

17. The computer-readable medium of claim 12, wherein instruction f) is repeating b) to e) for each region to be characterized in a plurality of intravascular ultrasound images; and
wherein determining the size of at least one of the tissue types comprises determining an absolute volume of at least one of the tissue types in a selected portion of the at least one intravascular ultrasound image using the tissue characterizations of the regions in the selected portion.

18. A tissue classifier, comprising
a plurality of detector arrays for each of a plurality of tissue types, wherein each detector array comprises a plurality of detectors and each detector comprises a plurality of tissue type-assigned intravascular ultrasound (IVUS) spectra, wherein a plurality of the tissue type-assigned IVUS spectra of each detector correspond to a tissue type of the detector and a plurality of the tissue type-assigned IVUS spectra correspond to other tissue types; and
a processor configured to execute processor-readable instructions that enable actions, including:
a) comparing an input IVUS spectrum of a region in the at least one intravascular ultrasound image to the tissue type-assigned IVUS spectra of each of the plurality of detectors for each of the plurality of detector arrays;
b) determining, for each of the plurality of detectors of each of the plurality of detector arrays, whether the input IVUS spectrum corresponds to the tissue type of the detector based on the comparisons of the input IVUS spectrum to the tissue type-assigned IVUS spectra for that detector;
c) for each of the plurality of detector arrays, combining results of the plurality of detectors of the detector array to produce an array result;
d) combining the array results for the plurality of detector arrays to provide a tissue characterization of the region from the plurality of tissue types;
e) repeating a) to d) for each region to be characterized in the at least one intravascular ultrasound image; and
f) determining a size of at least one of the tissue types in a selected portion of the at least one intravascular ultrasound image using the tissue characterizations of the regions in the selected portion.

19. The tissue classifier of claim 18, wherein the actions further comprise displaying one or more of the at least one intravascular ultrasound image with an indication of the tissue characterization of one or more regions of the at least one intravascular ultrasound image that is displayed and an indication of the size of at least one of the tissue types in the selected portion of the at least one intravascular ultrasound image that is displayed.

20. An imaging device, comprising:
a catheter configured and arranged for insertion into a patient;
a transducer disposed on the catheter and configured and arranged to produce ultrasound signals and receive backscattered signals;
a processor coupled to the transducer and configured and arranged to receive the backscattered signals from the transducer and to generate from the backscattered signals an image; and
the tissue classifier of claim 18.

21. The imaging device of claim 20, wherein the processor coupled to the transducer is also the processor of the tissue classifier.

22. The imaging device of claim 20, further comprising a display configured and arranged to display the image from the processor coupled to the transducer and to display the tissue characterization of the tissue classifier and the indication of the size of at least one of the tissue types in the selected portion of the at least one intravascular ultrasound image that is displayed.

* * * * *